United States Patent
Mohapatra et al.

(10) Patent No.: US 7,371,738 B2
(45) Date of Patent: May 13, 2008

(54) METHOD OF TRANSDERMAL DRUG DELIVERY USING HYALURONIC ACID NANOPARTICLES

(75) Inventors: Shyam S. Mohapatra, Tampa, FL (US); Bishwabhusan Sahoo, Champaign, IL (US); Arun Kumar, Tampa, FL (US); Sumita Behera, Irving, TX (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 11/279,956

(22) Filed: Apr. 17, 2006

(65) Prior Publication Data

US 2007/0036728 A1 Feb. 15, 2007

Related U.S. Application Data

(60) Provisional application No. 60/671,892, filed on Apr. 15, 2005.

(51) Int. Cl.
*A01N 43/04* (2006.01)

(52) U.S. Cl. ............... 514/54; 536/53; 536/123; 424/9.34; 424/489; 424/499; 424/501; 424/646; 977/788; 977/797; 977/798; 977/801; 977/930

(58) Field of Classification Search ............... 424/9.34, 424/489, 499, 646, 448, 501, 647, 648, 635; 977/930, 788, 810, 797, 798, 801; 536/53, 536/123; 514/54
See application file for complete search history.

(56) References Cited

U.S. PATENT DOCUMENTS 5,629,021 A * 5/1997 Wright .................. 424/489
6,576,221 B1 * 6/2003 Kresse et al. ............ 424/9.322
2004/0127459 A1 7/2004 Dehayza et al.
2005/0266093 A1 12/2005 Mohapatra
2006/0040892 A1 * 2/2006 Hu et al. .................. 514/54

FOREIGN PATENT DOCUMENTS

WO 2004074314 A2 2/2004
WO 2004112758 A1 12/2004

* cited by examiner

*Primary Examiner*—Yvonne Eyler
*Assistant Examiner*—Sudhakar Katakam
(74) *Attorney, Agent, or Firm*—Michael M. McGaw; Smith & Hopen, P.A.

(57) ABSTRACT

The present invention relates to the development of a hyaluronic acid and hyaluronic acid hybrid nanoparticle systems for the administration of active molecules, peptides, DNA and/or other hydrophilic or hydrophobic molecules, the composition of hyaluronic acid and hyaluronic acid hybrid nanoparticle systems, and the procedure for their development and use. These nanoparticles are made up of hyaluronic acid in salt form, preferentially the sodium salt of the polymers or hybridized with magnetic Fe particles. The nanoparticles are basically from natural polymers, biocompatibles and biodegradables. The nanoparticles allow the controlled release of the active molecules they transport and their orientation towards the target tissues. The present invention teaches a procedure to elaborate particles of hyaluronic acid with a diameter less than 180 nm., that incorporate an active ingredient, independent of its hydrophilic or hydrophobic nature. Procedures to produce the particles are described. The present invention will be useful in methods of transdermal drug delivery using hyaluronic acid nanoparticles, among other uses.

7 Claims, 5 Drawing Sheets

METHOD OF TRANSDERMAL DRUG DELIVERY USING HYALURONIC ACID NANOPARTICLES

CROSS REFERENCE TO RELATED APPLICATIONS

This application claims priority to currently abandoned U.S. Provisional Patent Application 60/671,892, entitled, "A Method of Transdermal Drug Delivery Using Hyaluronic Acid Nanoparticles", filed Apr. 15, 2005.

FIELD OF INVENTION

This invention relates to transdermal drug delivery systems. More specifically, this invention relates to the development of a novel hyaluronic acid based-nanoparticle, and hybrid particles thereof, which can be specifically targeted to disease cells for many diseases.

BACKGROUND OF INVENTION

Hyaluronic acid ("HA") is a polysaccharide composed of D-glucuronic acid and N-acetyl-D-glucosamine. It has been used for transdermal drug delivery. HA is found on mammalian cell surfaces, in the basic extra cellular substances of the connective tissues of vertebrates, synovial fluid of joints, vitreous of the eye, tissue of human umbilical cord and in cocks' comb. It is the main component of the extracellular matrix. HA plays an important role in the mechanical support of the cell of many tissues, such as the skin, the tendons, the muscles and cartilage. Since HA binds to its receptor, CD44, on metastatic melanoma cells and hyaluronan is taken up through CD44 and degraded inside the cells, these particles are uniquely suited to specifically detect and destroy these metastatic cells. Like other nanoparticles, HA has several advantages as a carrier of genes, drugs or proteins to these cells. It is less immunogenic or non-immunogenic. Its molecular structure is common in all mammals (HA plays a major component of the extracellular matrix of all tissues). And, derivatives of HA have unique properties for specific biomedical applications without any adverse effects.

HA and its salts are currently being used in various therapies, such as for arthropathies, by intraarticular injection, in opthalmic surgery for intraocular lens implantation, to promote wound healing in various tissues, or, in derivatized and/or crosslinked form, to manufacture thin films or sponges, which are used for tissue separation or other biomedical applications (for review see Band). Strategies have included esterification of HA, acrylation of HA and cross-linking of HA using divinyl sulfone or glycidyl ether. However, these modifications result in decreased solubility in water and/or the chemical reaction strategies used are not designed for cross-linking of HA under physiological conditions (in an aqueous environment, at pH 6.5-8.0). There exists a need in the art for the development of HA nanoparticles. There also exists a need in the art that such particles to be composed of only hyaluronic acid rather than a mixture of two or more polymers.

The invention provides the development of nanoparticles composed of HA, which can be encapsulated and formulated with various peptide, DNA and small molecular drugs for cell specific drug delivery.

SUMMARY OF INVENTION

The present invention relates to the development of a hyaluronic acid and hyaluronic acid hybrid nanoparticle systems for the administration of active molecules, peptides, DNA and/or other hydrophilic or hydrophobic molecules, the composition of hyaluronic acid and hyaluronic acid hybrid nanoparticle systems, and the procedure for their development and use. These nanoparticles are made up of hyaluronic acid in salt form, preferentially the sodium salt of the polymers or hybridized with magnetic Fe particles. The nanoparticles are basically from natural polymers, biocompatibles and biodegradables. The nanoparticles allow the controlled release of the active molecules they transport and their orientation towards the target tissues. The present invention teaches a procedure to elaborate particles of hyaluronic acid with a diameter less than 180 nm., that incorporate an active ingredient, independent of its hydrophilic or hydrophobic nature. Procedures to produce the particles are described. The present invention will be useful in methods of transdermal drug delivery using hyaluronic acid nanoparticles, among other uses.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
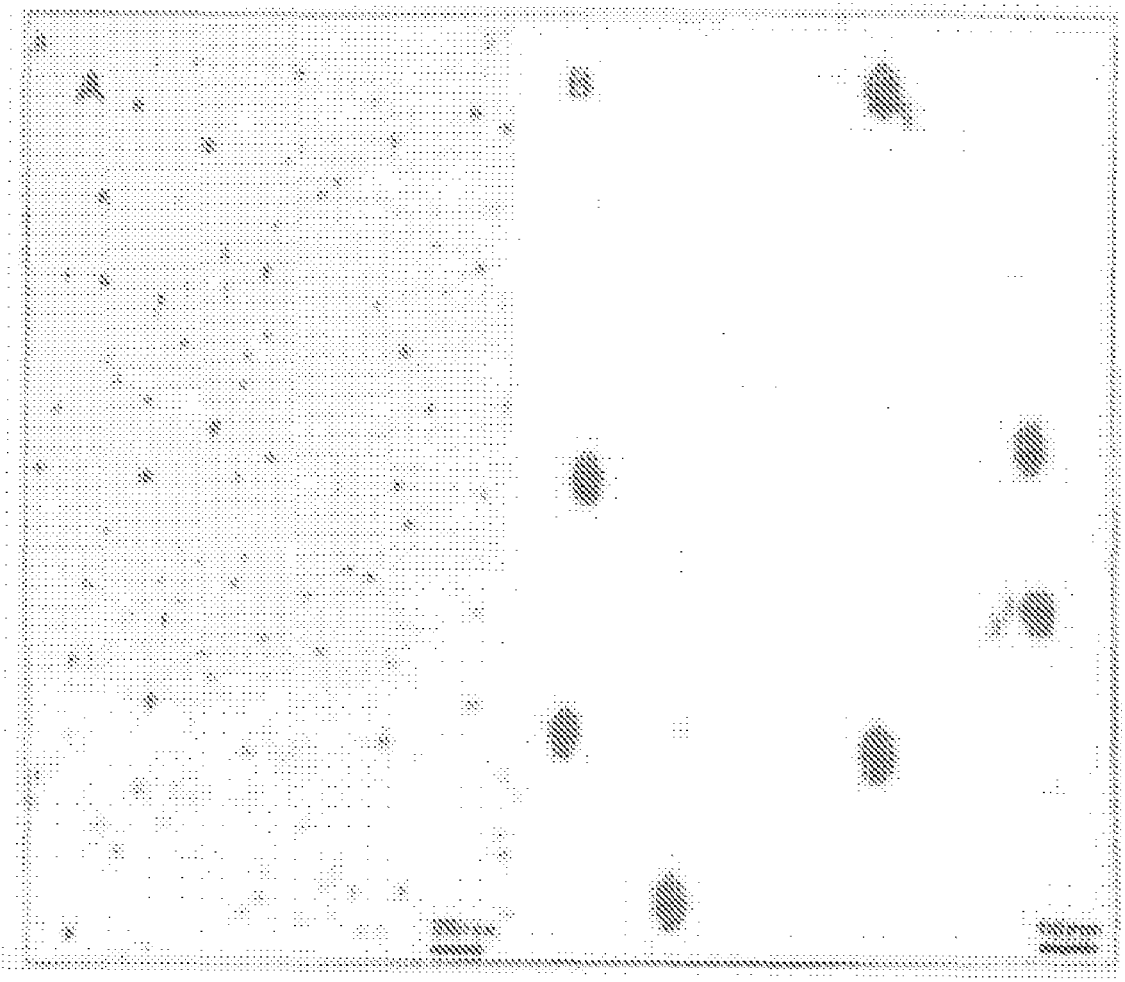
FIG. 1 is a transmission electron micrograph image of an HA nanoparticle. In (A) the nanoparticles are shown at 18,000× while in (B) the nanoparticles are shown at 62,000× magnification.

The disclosed invention is a novel hyaluronic acid nanoparticle and methods of using and producing the disclosed hyaluronic acid nanoparticle.

The nanoparticles were prepared by self-assembling micro-emulsions techniques and were encapsulated using surfactants. Briefly, Hyaluronic acid ("HA") (from Sigma) and a dihydrazide were mixed, homogenized and incubated with the crosslinking reagent in an aqueous solution. The aqueous solution was added to a non-polar organic solvent and a biodegradable surfactant to form an oil-in-water type emulsion. The pH of the reaction was lowered to allow the intramolecular and intermolecular crosslinking reaction and the subsequent formation of nanospheres.

EXAMPLE 1

Preparation of Nanoparticle from Hyaluronic Acid Sodium Salt Isolated from Human Umbilical Cord (CAS 9067-32-7)

In a typical experiment, the procedure comprises the following stages: a) Preparation of an aqueous solution of a salt of hyaluronic acid, in a concentration of 6 mg/ml; b) preparation of an aqueous solution of a hydrazide, in a concentration 3 mg/ml (The hydrazide used is oxalic hydrazide); c) preparation of the sorbitan monosterate (1-2% w/v); d) addition of the hydrazide solution (3 mg/ml) to the solution of hyaluronic acid, followed by injection of 1-(3-dimethvlaminopropyl)-3-ethylcarbodilmide hydrochloride (EDCL) solution (2.7 mg/ml); e) addition of the surfectent solution; and f) mixing under magnetic stirring (1200-100 rpm). lowering the pH and maintaining the stirring overnight, which will produce the nanoparticles.

The work-up of the nanoparticles was as follows: pH was increased to the range of 8-9, followed by the addition of alcohol to precipitate the nanoparticle. The precipitated nanoparticles were kept in drying oven at 25° C. for six hours to dry. The resulting nanoparticles can be kept in the refrigerator for storage.

EXAMPLE 2

Encapsulation of FITC to the HA-Nanoparticle

In a typical experiment, the procedure of the encapsulation of the FITC comprises the following stages: a) Preparation of an aqueous solution of a salt of hyaluronic acid in a concentration of 6 mg/ml; b) preparation of an aqueous solution of a hydrazide in a concentration 3 mg/ml; c) preparation of the sorbitan monosterate (1-2% w/v); d) addition of FITC (0.2% of the surfactant solution) to the sorbitan monosterate solution; e) addition of a hydrazide solution (3 mg/ml) to the solution of hyaluronic acid, followed by injection of EDCl solution (2 7 mg/ml); f) addition of surfactant solution with FITC; and g)mix under magnetic stirring (1200-100 rpm), which will form the oil-water emulsion and will allow to mix the HA, reagents, FITC etc. Further the reaction will proceed by lowering the pH and maintaing the stirring (800-900 rpm for overnight, which will produce the nanoparticles encapsulated with FITC. The flask should be covered with aluminum foil to avoid the light. The work-up of the nanopartieies were as follows: pH increased to 8-9, followed by addition of alcohol to precipitate the nanoparticles at 25° C. The precipitated nanoparticles were kept in drying oven at 25° C. for six hours to dry. Keep in the refrigerator for storage with aluminum cover for protection from the light.

EXAMPLE 3

Encapsulation of Active Substance ANP to the HA-Nanoparticle

In a typical experiment, the procedure of the encapsulation of the ANP comprises the following stages a) Preparation of an aqueous solution of a salt of hyaluronic acid in a concentration of 6 mg/ml followed by the addition of 0.5 mg of ANP to the solution (stir the solution well at 10-15° C. for the complete mixing of both HA and ANP peptide into water); b) preparation of an aqueous solution of a hydrazide in a concentration 3 mg/ml; c) preparation of the sorbitan monosterate (1-2% w/v); d) addition the hydrazide solution (3 mg/ml) to the solution of hyaluronic acid-ANP mixture, followed by injection of EDCl solution (2.7 mg/ml); e) addition of the surfactant solution; and f) mixing under magnetic stirring (1200-100 rpm), which will form the oil-water emulsion and will allow to mix the HA, ANP, reagents etc. Further the reaction will proceed by lowering the pH, lowering the temp to 10° C. and mnaintaing the stirring (800-900 rpm) for 6-8 hours, which will produce the nanoparticles encapsulated with ANP. The flask should be covered with aluminium foil to avoid the light.

The work-up of the nanoparticles were as follows: pH increased to 8-9, followed by addition of alcohol to precipitate the nanoparticle at 25° C. The precipitated nanoparticles were kept in drying oven at 25° C. for six hours to dry. Keep in the refrigerator for storage with aluminum cover for protection from light.

EXAMPLE 4

Encapsulation of the Active Substance Green Fluorescence Protein (GFP) in the HA Nanoparticle In a typical experiment, the procedure of the encapsulation of the GFP comprises of the following stages: a) Preparation of an aqueous solution of a salt of hyaluronic acid, in a concentration of 6 mg/ml followed by addition of 0.5 mg of GFP to the solution, (stir the solution well at 10-15° C. for the complete mixing of both HA and GFP peptide into water); b) preparation of an aqueous solution of a hydrazide in a concentration 3 mg/ml; c) preparation of the sorbitan monosterate (1-2% w/v); d) addition of the hydrazide solution (3 mg/ml) to the solution of hyaluronic acid-GFP mixture, followed by injection of EDCl solution (2.7 mg/ml); e) addition of the surfactant solution; and f) mixing under magnetic stirring (1200-100 rpm), which will form the oil-water emulsion and will allow to mix the HA, GFP, reagents etc. Further the reaction will proceed by lowering the pH, lowering the temp to 10° C. and maintaining the stirring (800-900 rpm) for 6-8 hours, which will produce the nanoparticles encapsulated with GFP. The flask should be covered with aluminium foil to avoid the light.

The work-up of the nanoparticles were as follows: pH increased to 8-9 and followed by addition of alcohol to precipitate the nanoparticle at 25° C. The precipitated nanoparticles were kept in drying oven at 25° C. for six hour to dry. Keep in the refrigerator for storage with aluminum cover from the protection of light.

EXAMPLE 5

Preparation and Modification of Size of the HA Particle

The size of the particles were further reduced to 10-40 nm. In a typical experiment, prior to emulsion crosslinking, the HA was hydrolyzed using dil. hydrochloric acid, which can significantly decrease its molecular weight (20-40 kD) and then can be used for further nanoprticle preparation using the method, or methods, described above. In this condition, we saw the using the 1.5N HCl and hydrolyzing the HA for 4 hrs at room temperature, followed by crosslinking using the procedure described in example 1, which forms the nanoparticle of the reduced size up to 10-40 nm. The particles were characterized by TEM and AFM studies. If these low molecular weight HA particles retain their biological activity as evidenced from their binding to CD44 expressing cells, then they will be further modified as described above.

Development of HA-Fe2O3 hybrid nanoparticle:

EXAMPLE 6

Synthesis of Fe2O3 Nanoparticles

Synthesis of Fe2O3 nanoparticles was performed in aqueous medium without surfactants. The Fe2O3 nanoparticles have an average diameter less than 40 nm and narrow size distributions. The colloidal suspensions of the magnetite can then be directly oxidized by aeration to form the colloidal suspension of Fe2O3 nanoparticles. To synthesize homogeneous nanoparticles and compositions it is important to perform the reaction in basic aqueous solutions with molar ratio of Fe (II)/Fe (III)=1:2. DI water (resistance 17.8MΩ) were used to dissolve the components in solutions with vigorous stirring. The resulting solution was precipitated with spray method in aqueous medium. After the formation of nanoparticles, the nanoparticles were washed several times with DI water to remove the untreated components.

Reaction Involved:

FeCl2+FeCl3→Fe3O4→Oxidation→Fe2O3

EXAMPLE 7

Synthesis of Hybrid HA-Fe2O3

First, a 1 mL solution of HA nanoparticles was attached to the colloidal solution of Fe2O3.

The hybrid nanoparticles were synthesized by adding 0.50 mL of a freshly prepared 1 mM aqueous solution of Fe2O3 to 2.5 mL of the colloidal HA under vigorous stirring. The solution was left to stand for 15 min to achieve hydrolysis of the surface groups and formation o vitreophilic nanoparticles. Second, 2 mL of acid solution was added to the functionalized solution under vigorous stirring, and the mixture was allowed to stand for at least 24 h to produce an HA- Fe2O3 hybrid nanoparticles. The HA-Fe2O3 was then washed with deionized (DI) water several times to remove an excess components. The HA-Fe2O3 colloidal hybrid nanoparticles were added to a mixture of 1 mL of ethanol and 1 mL of NH4OH (25%) under vigorous stirring, and the solution left under mild magnetic stirring for at least 2 h at room temperature. The solution was then evaporated and dries under vacuum. The average diameter of the HA-Fe2O3 nanoparticles were found to be 80-85 nm.

Characterization of HA nanoparticles and their derivatives:

Characterization is initially by TEM, AFM, NMR and IR spectroscopic techniques. They will be characterized for size using a Zeta Sizer and for physical characteristics using spectroscopic and microscopic analyses. The diameter, zeta potential and molecular weight of the nanoparticles will be determined as mean particle diameter and size distribution using a Zeta Sizer. The zeta potential will be determined by laser doppler velocimetry. The derivatized products will be also characterized by NMR. Proton (1H) and carbon (13C) NMR spectra will be recorded on a Varian 400 at 400 and 100.13 MHz, respectively. The chemical shifts in parts per million (ppm) for 1H and 13C NMR spectra will be referenced relative to tetramethylsilane (TMS) at 0.00 ppm, respectively. Proton (1H), carbon (13C), COSY and DEPT experiments will be carried out to determine the substitution and selectivity of the reactions. IR spectroscopy will also be used to determine the functionalization of HA. Dynamic light scattering, Transmission electron microscope (TEM) will be used to determine the size distribution of the nanospheres pre and post-modification.

Figure 2:
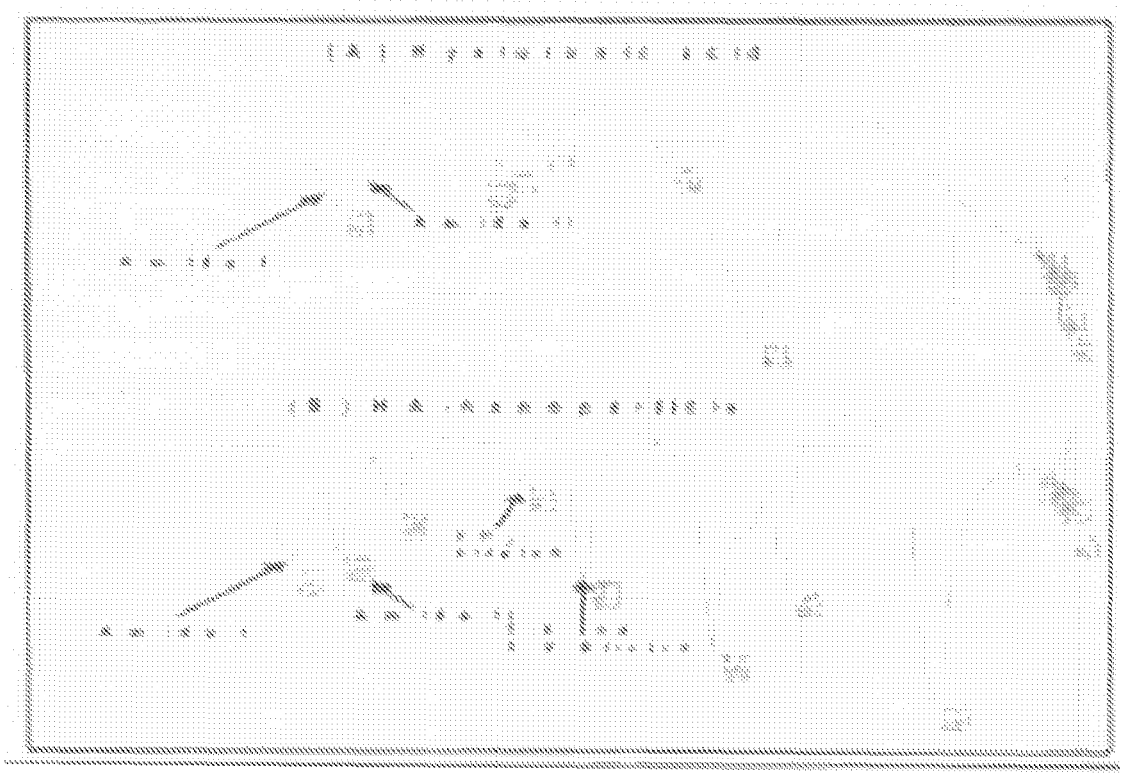
FIG. 2 depicts the IR spectra of HA (upper panel) and of the HA nanoparticle crosslinked with dihydrazide (lower panel). The lower panel shows that the amide I and amide II band at 1676 and 1601 cm-1 is enhanced as compared to the starting HA, which indicates cross-linking reaction. Also, the peak at 1272 and 1359, which correspond to the C—N/C—O and CH2 stretch indicate the presence of the pendant hydrazide group.
Figure 3:
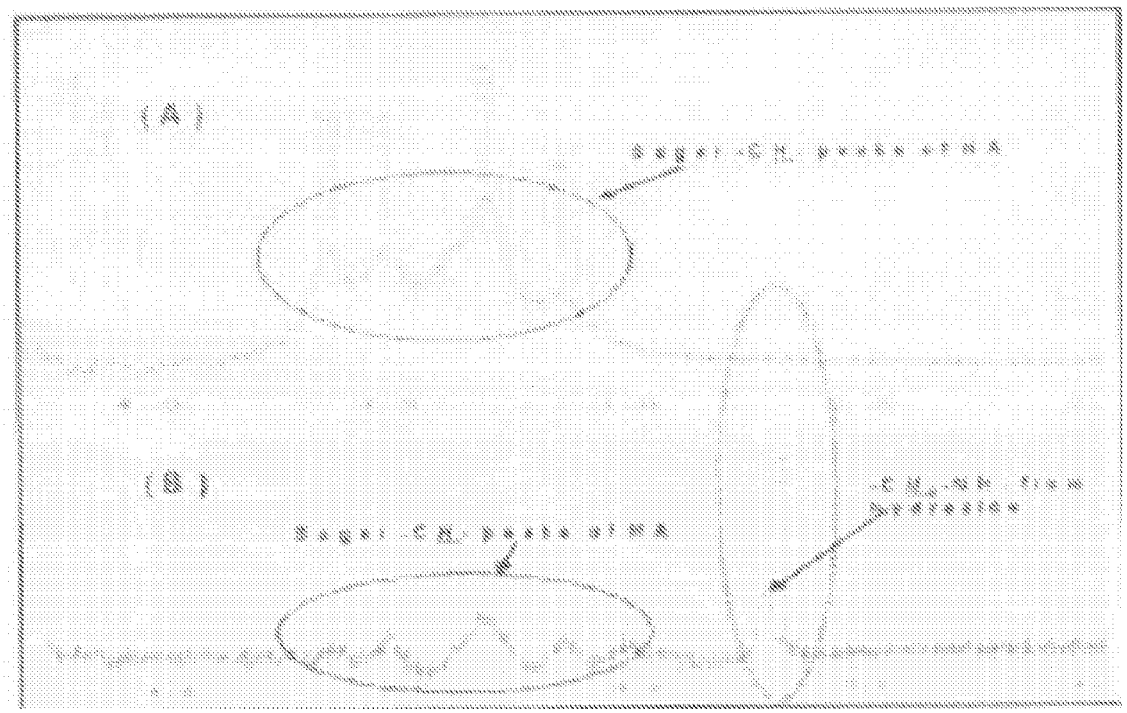
FIG. 3 depicts the 1H NMR spectra of samples. The 1H NMR spectra were measured in D2O solutions using VARIAN UNITY 400 spectrometer operating at frequencies of 400 MHz. No standard TMS were used for this measurement. Samples were kept in Wilmad 5 mm NMR tubes in D2O for 4 hours prior to the experiment. The NMR spectra were accumulated at 27OC. The upper panel corresponds to the proton NMR spectra of HA (64 scan) and the lower panel shows the FIG. 4 depicts an AFM image of HA-Fe2O3 hybrid nanoparticles.
Figure 4:
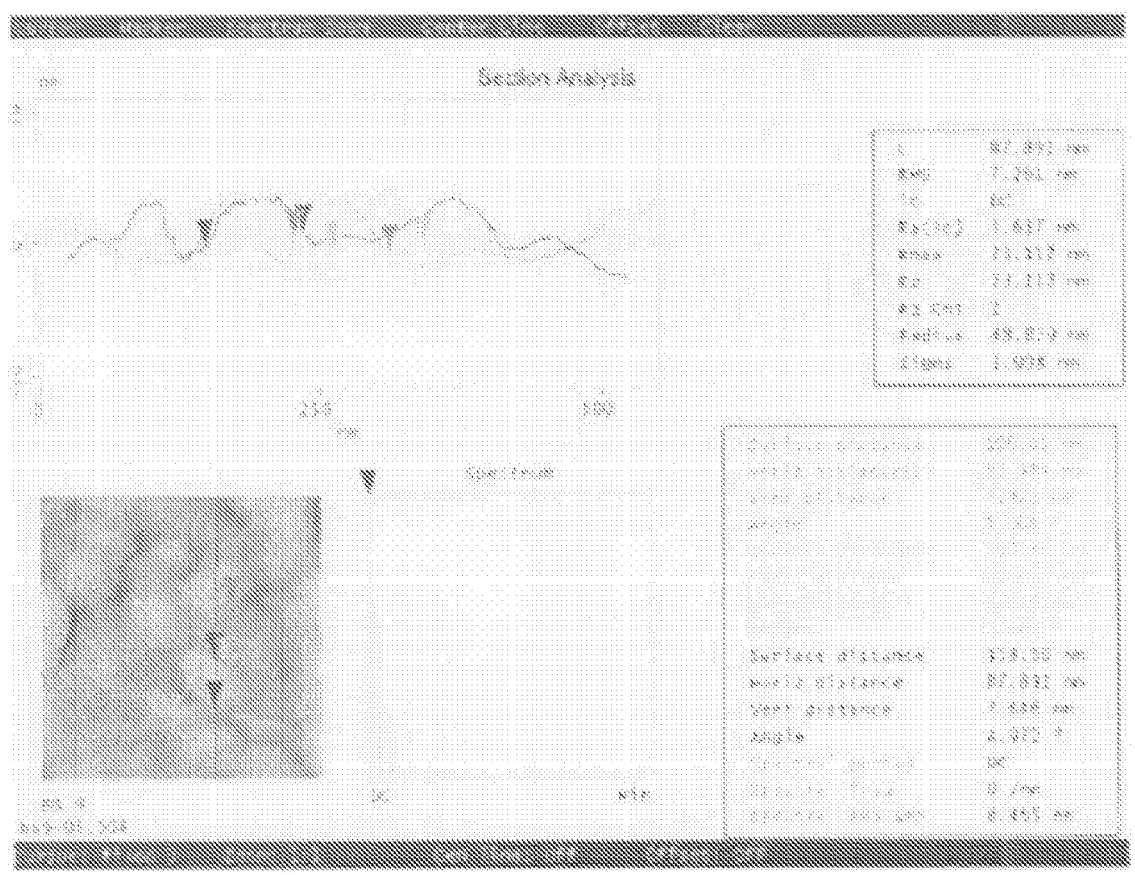

The HA nanoparticles were characterized by transmission electron microscope (TEM), NMR, FT-IR and atomic force microscope. As show in FIGS. 1-2 a TEM analysis of the HA nanoparticle complexed with FITC, gives the particle size of diameter ranging from 80-160 nm. Analysis by FT-IR confirmed cross linking reaction between the HA polymers and the outer surface containing the hydrazide pendant group. NMR analysis indicated crosslinking and modification of HA. FIG. 4 shows AFM of image of HA- Fe2O3 hybrid nanoparticle (sectional image), showing the average diameter of 80-85 nm.

EXAMPLE 8

HA Nanoparticles Support Transfer of Peptides and DNA into the Cells

Figure 5:
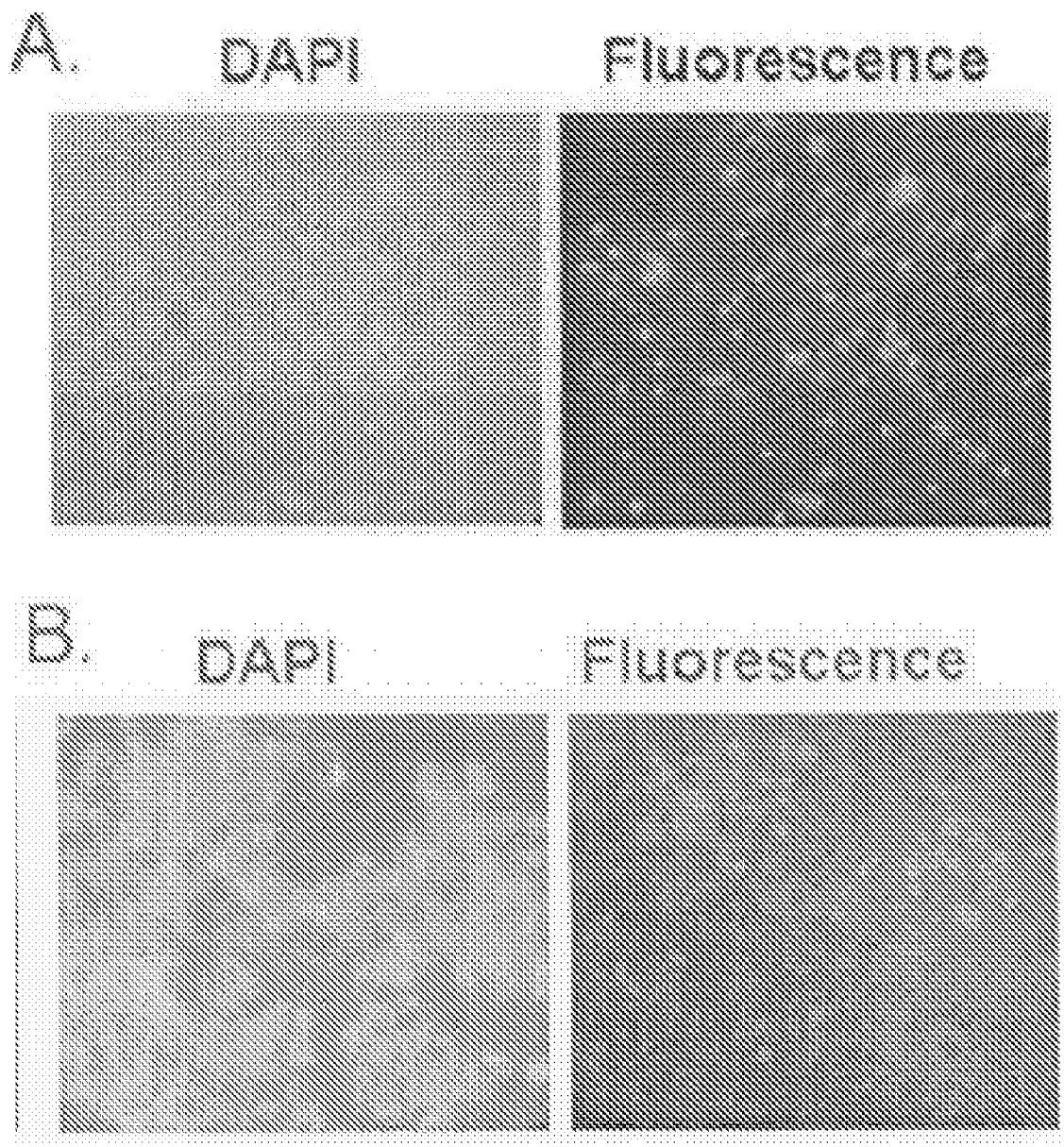
FIG. 5 is a series of photographs demonstrating peptide and DNA delivery of HA nanoparticles. HEK293 cells were incubated with HA nanoparticles encapsulating either NP-73-102 peptide-labeled with FITC (upper panel) or plasmid encoding DS_Red (lower panel) Cells were observed under the fluorescence microscope after 72 hours. Cells were stained with nuclear stain DAPI to show the presence of live cells.

To examine potential of HA nanoparticles in peptide and Gene transfer vas examined using human embryonic kidney (HEK293) epithelial cells. First, H.EK293 cells were in with nanoparticles of HA encapsulating ANP peptide linked with FITC and the cells were examined under fluorescence microscope at 24, 48 and 72 h after incubation. The results showed that almost all cells were capable of taking in these particles (FIG. 5A). Also, HEK293 cells were transfected with HA nanoparticles encapsulating plasmid DNA, which encodes DS-Red protein. The results showed that the cells were capable of nanaparticle carried DNA (FIG. 5B).

The present invention is an It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for the preparation of hyaluronic acid nanoparticles comprising the steps of:
   mixing hyaluronic acid and a hydrazide with a cross-linking agent in an aqueous solution;
   adding a non-polar organic solvent and a surfactant to form an oil-in-water emulsion; and
   lowering the pH of the reaction to allow intramolecular and intermolecular cross-linking.

2. The method according to claim 1 further comprising the steps of:

raising the pH of the solution following cross-linking to the range of about 8 to about 9; and precipitating the nanoparticles from the solution by the addition of alcohol.

3. The method according to claim 1 further comprising the step of adding hydrochloric acid to the hyaluronic acid prior to forming the oil-in-water emulsion.

4. The method according to claim 1 wherein the hydrazide is oxalic hydrazide.

5. The method according to claim 1 wherein the surfactant is sorbitan monosterate.

6. The method according to claim 1 wherein the cross-linking agent is 1-(3-dimethylaminopropyl-3-ethylcarbodiimide hydrochloride.

7. A method for the preparation of hybrid hyaluronic acid $Fe_2O_3$ nanoparticles comprising the steps of:

mixing hyaluronic acid and a hydrazide with a cross-linking agent in an aqueous solution;

adding a non-polar organic solvent and a surfactant to form an oil-in-water emulsion; and lowering the pH of the reaction to allow intramolecular and intermolecular cross-linking;

adding a colloidal solution of $Fe_2O_3$;

adding an acid solution; and precipitating the resultant HA-$Fe_2O_3$ nanoparticles.

* * * * *